(12) United States Patent
Klein

(10) Patent No.: US 7,074,948 B1
(45) Date of Patent: Jul. 11, 2006

(54) COMPOSITIONS CONTAINING GUERBET LANOLIN ESTERS AND FREE LANOLIN ALCOHOL USEFUL IN PERSONAL CARE APPLICATIONS

(75) Inventor: Kenneth Klein, Fairlawn, NJ (US)

(73) Assignee: Zenitech LLC, Old Greenwich, CT (US)

( * ) Notice: Subject to any disclaimer, the term of this patent is extended or adjusted under 35 U.S.C. 154(b) by 76 days.

(21) Appl. No.: 11/002,347

(22) Filed: Dec. 3, 2004

(51) Int. Cl.
*C11C 3/00* (2006.01)

(52) U.S. Cl. ...................................... 554/169; 424/70.1

(58) Field of Classification Search ................ 554/169; 424/70.1
See application file for complete search history.

(56) References Cited

U.S. PATENT DOCUMENTS 6,630,134 B1    10/2003   Klein et al.

*Primary Examiner*—Deborah D. Carr

(57) ABSTRACT

The present invention relates to the cosmetic use of certain esters, prepared by the reaction of a Guerbet alcohol and lanolin. The result is a cosmetically elegant ester and lanolin alcohol which is a highly functional material in skin care. These compositions provide conditioning effects when applied to the hair and skin.

10 Claims, No Drawings

COMPOSITIONS CONTAINING GUERBET LANOLIN ESTERS AND FREE LANOLIN ALCOHOL USEFUL IN PERSONAL CARE APPLICATIONS

FIELD OF THE INVENTION

The present invention relates to use of certain Guerbet lanolin esters, prepared by the reaction of a Guerbet alcohol and lanolin for use in personal care applications. These materials are useful in preparation of cosmetic products where their ability to make custom chosen melting point, and custom chosen softness and delivery of lanolin alcohols in a cosmetically elegant base. The reaction renders the lanolin smooth and cosmetically appealing and provides a melting point suitable for application to the skin. Lanolin is a sticky unappealing material.

BACKGROUND OF THE INVENTION

The present invention relates to compositions that result from the transesterification of lanolin with a Guerbet alcohol. The composition has free lanolin alcohol and Guerbet ester that delivers efficiently and thoroughly to the skin.

U.S. Pat. No. 6,630,134 issued Oct. 7, 2003 to Kenneth Klein, incorporated herein by reference discloses Guerbet wax esters in personal care applications. That invention relates to the cosmetic use of certain reconstituted wax esters, prepared by the reaction of a Guerbet alcohol and a natural high molecular wax ester selected from the group consisting of beeswax, candelillia, and carnauba wax. These materials are useful in making waxes with specific melting points and degrees of hardness for personal care applications like lipsticks, and a variety of other applications personal care formulations. The waxes provide conditioning effects when applied to the hair and skin.

U.S. Pat. No. 6,087,522 issued Jul. 11, 2000 to O'Lenick, Jr., incorporated herein by reference, discloses Silicone lanolin esters. Specifically, lanolin esters of silicones are prepared by reacting a carboxy silicone and lanolin alcohol to form an ester. The resultant products are useful as highly water resistant lubricating coatings for skin. Specifically, the carboxy silicone reacts with the lanolin alcohol in the lanolin ester, exhausting this very important active material.

Lanolin has been used for many years in personal care applications. Lanolin (CAS number 8006-54-0) is a pale yellow paste, obtained from the wool of sheep. It is a waxy ester. Lanolin is used as a topical treatment on skin. Since lanolin is very water insoluble and difficult to formulate into many products, it has been derivatized. Lanolin has been ethoxylated to make water soluble ethoxylates. Generally 75 moles of ethylene oxide is added to obtain the desired solubility. While the ethoxylation provides the desired solubility, the substantivity to the skin and the water resistant properties are sacrificed.

Lanolin alcohol is composed of;

| Component | % by weight | Range (%) |
|---|---|---|
| Cholesterol | 34.5 | 29.5–39.5 |
| Aliphatic alcohols | 25.0 | 12.5–37.5 (having 18 to 30 carbon atoms) |
| Diols | 12.5 | 10.0–15.0 |
| Lanosterol | 10.0 | 3.0–17.0 |
| 3-beta-hydroxy-7-keto-lanst-8-ene | 10.0 | 5.0–15.0 |
| Dihydrolanesterol | 8.0 | 4.0–12.0 |

We have surprisingly found that the Guerbet branched alcohol reacts with the lanolin ester forming a Guerbet ester and freeing up the desirable alcohol portion of the ester, providing a product we call Lanolin Butter. The reaction mixture, results in maintaining the active alcoholic portion of the lanolin and at the same time enhanced skin feel, melt charactstics and giving a product with altered melting point and skin feel.

U.S. Pat. No. 4,066,789 to Mores, et al. issued Jan. 3, 1978 describes Blends of lanolin wax and esters of aliphatic polyols and fatty acids. The patent incorporated herein by reference states: "Lanolin (refined and neutralized wool grease) has a unique combination of emulsifying ability, emolliency and ability to absorb water which makes it extremely useful in a variety of cosmetic and pharmaceutical formulations. Numerous products such as hand, face and body creams and lotions, lipsticks and lip glosses, shampoos, hair preparations, body and both oils, make-ups, facial masks and suntan preparations utilize lanolin to impart desirable characteristics to the formulation. Lanolin is also useful in the textile industry as a softening agent and finds some use in industrial lubricating applications because of the anti-corrosive and rust preventive properties of the compound.

Anhydrous lanolin U.S.P. is described as a yellow, tenacious unctuous mass having a slight characteristic odor. It is insoluble in water but mixes without separation with about twice its weight of water. The product has a slight acid value and melts at about 36–42° C. Lanolin is a complex mixture of long-chain esters derived from higher alcohols, predominantly fused ring alcohols (sterols), and fatty acids and is one of the few natural fatty materials that contains a high percentage (.about.50%) of esterified hydroxy acids.

U.S.P. lanolin is not without some disadvantages in certain formulations. For example, a problem can arise due to incompatibility of the lanolin with hydrocarbon oils, the product may exhibit an undesirable amount of tackiness or emulsion stability may be unsatisfactory. For these reasons various derivatives of lanolin such as the ethoxylated and acylated derivatives have been developed. Lanolin can also be fractionated to obtain a more cosmetically elegant liquid form which has superior properties and improved compatibility with mineral oils. There has been a long felt need for a product that can have both the desired aesthetics and functionality that is found in the lanolin alcohol fraction. U.S. Pat. No. 4,066,789 proposes blends to overcome the shortcomings of lanolin, and thereby teaches away from our invention.

U.S. Pat. No. 4,069,347 issued Jan. 17, 1978 to McCarthy, et al, discloses compositions of quaternary ammonium derivatives of lanolin acids. Specifically they teach; "The lanolin quats used for this invention are derived from lanolin acids, preferably, refined lanolin acids, which are reacted with a diamine having one tertiary amine group with the remaining amine function being either a primary or secondary amine. Dimethylaminopropylamine, diethylaminopropylamine, dimethylaminoethylamine and diethylaminoethylamine are especially useful for this purpose". The products are made from the fatty acids of lanolin, not the highly desirable lanolin alcohol derivatives, again teaching away from our invention. Lanolin is the unctuous secretion of the sebaceous glands of sheep which is deposited onto the wool fibers. It softens the fleece and serves to protect the fleece against the elements. It is a wax, not a fat. It is a complex mixture of esters, di-esters and hydroxy esters of high molecular weight lanolin alcohols (69 aliphatic alcohols ($C_{12}$–$C_{36}$) and 6 sterols have been identified in lanolin) and high molecular weight lanolin acids (approximately 138 acids (C.sub.7–C.sub.41) have been identified in lanolin). Lanolin is a by-product of the wool-scouring industry.

Wool grease constitutes 10–15% of the weight of sheared wool, depending on the breed of sheep, anatomical area sheared, inner and outer fleece, and season. The average composition of Australian fleeces is 11–16% grease, 6–8% suint (potassium salts of various organic and inorganic acids in the sweat), 10–12% water, 8–19% dirt and 49–61% wool fiber. One hundred pounds of wool yield about 2 to 4 pounds of lanolin. Lanolin is recovered by wool-scouring, followed by separation and purification which may include acid cracking or centrifugal washing, neutralization, removal of soaps, filtration, bleaching and deodorization.

OBJECT OF THE INVENTION

It is the object of the present invention to provide unique cosmetic compositions that can be made to a variety of melting points and hardness for specific applications, and have the active ingredients of lanolin alcohol present in a very suitable delivery base. These materials are applied to the skin and hair to provide softening and conditioning effects, and maintaining the functional attributes provided by the lanolin alcohol portion. These materials are applied to the skin and hair in an effective skin repairing concentration. The concentration ranges from 0.1% to 65% by weight of the cosmetic product.

Lanolin is an effective emollient, which by subjective evaluation, effects softening and improvement of dry or rough skin caused by lack of sufficient natural moisture retention. Idson, B. ("What is a moisturizer?", Amer. Perf. Cosm. 87: 33–35 (August 1972)) reported that lanolin causes the water in the skin to build up to its normal level of 10–30% by retarding, without completely inhibiting, trans-epidermal moisture loss.

A relative quantitative evaluation of the occlusive effect of lanolin and other cosmetic materials on the transpiration of moisture from human skin was made by Powers et al. ("A study of the effect of cosmetic ingredients, creams and lotions on the rate of moisture loss from the skin", Proc. Sci. Sect. TGA, No. 28, 21–26 (December 1957)). In particular, lanolin was applied to the inner surface of the forearm (5.0–6.25 mg/cm.sup.2, equivalent to a film thickness of 54–68 microns), and was covered with a 28 mm diameter glass desiccators containing silica gel. The uptake of water was determined by weighing the miniature desiccators after specific time intervals. All results were obtained under conditions of zero relative humidity. Lanolin caused a 32% reduction in moisture loss from the skin and lanolin oil a 22% reduction, indicating a mild occlusive effect for these materials as opposed to the extreme barrier effect of petrolatum (48% reduction in moisture loss).

Unfortunately, lanolin, per se, is not satisfactory as a skin treatment product because of its high viscosity, tackiness, and high drag property, thereby making it aesthetically unacceptable to consumers and too difficult to spread onto the skin to be widely accepted.

Thus, historically, lanolin has been used as an auxiliary emulsifier in water-in-oil systems such as the traditional cold creams. In addition to performing as an auxiliary emulsifier, it improves the feel of oil and petrolatum base systems of this type and imparts elegance and a silky smooth texture to the film on the skin. It also modifies the moisture permeability of the extremely occlusive hydrocarbons used in these systems and permits some diffusion of water vapor through the film. This property is related to the fact that lanolin contains a high concentration of hydroxy fatty acid esters of which about 80% are branched. In this respect it resembles human sebum and can in fact duplicate many of the functions of that substance when applied to the skin in cosmetic formulations.

In humans, the branched chain fractions of sebum are at their greatest in the skin of the fetus and diminish with age, becoming much reduced in adults principally because these fatty acids are not derived from metabolism but are by-products of the actual keratinization process, a process which decreases with age. Lanolin can therefore be thought of as supplementing these reduced branched chain fatty acids and as a beneficial emollient, softening and superfatting agent. Lanolin alcohol in the Guerbet ester produced by trans-esterification accomplishes these desirable effects, while having a highly desirable cosmetic feel.

DETAILED DESCRIPTION OF THE INVENTION

The present invention is directed to a composition made by the trans esterification reaction of a Guerbet alcohol conforming to the following structure:

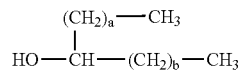

wherein;

a is an integer ranging from 3 to 11;

b is an integer ranging from 5 to 19, with the proviso that b=a+2;

and lanolin, wherein said trans esterification reaction is carried out at a temperature of between 180° C. and 200° C.

The invention is also directed to a process for conditioning hair and skin, which comprises contacting the hair or skin with an effective conditioning concentration of a composition made by the esterification reaction of a Guerbet alcohol conforming to the following structure:

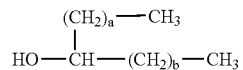

wherein a is an integer ranging from 3 to 11;

b is an integer ranging from 5 to 19, with the proviso that b=a+2;

with lanolin, wherein said esterification reaction is carried out at a temperature of between 180° C. and 200° C.

PREFERRED EMBODIMENT

In a preferred embodiment a is 3 and b is 5.

In a preferred embodiment a is 7 and b is 9.

In a preferred embodiment a is 9 and b is 11.

In a preferred embodiment a is 11 and b is 13.

In a preferred embodiment a is 13 and b is 15.

In a preferred embodiment a is 15 and b is 17.

In a preferred embodiment a is 17 and b is 19.

EXAMPLES

Lanolin

Lanolin is commercially available from a variety of sources the most important of which is The Fanning Corporation in Chicago Ill. Lanolin is a well defined natural product and has USP definition and specification.

| INCI (CTFA) NAME: | Lanolin |
|---|---|
| CAS NUMBER: | 8006-54-0 |

Lanolin is a yellow, tenacious, unctuous substance obtained from the wool of sheep, having a faint but characteristic odor.

Lanolin is classified chemically as a wax, being a complex mixture of naturally occurring esters and poly-esters of 33 high molecular weight alcohols (principally sterols) and 36 fatty acids. It is 98% ester minimum, of which the fatty alcohols and fatty acids comprise an approximately 50/50 ratio.

| Typical Composition of Lanolin | |
|---|---|
| Esters of sterols and triterpene alcohols | 35.4% |
| Esters of aliphatic alcohols | 23.7% |
| Monohydroxyesters of sterols and of triterpene and aliphatic alcohols | 20.0% |
| Di- and polyhydroxyesters and free diols | 7.9% |
| Free aliphatic alcohols | 5.6% |
| Free Sterols | 4.1% |
| Free hydrocarbons | 0.6% |
| Free fatty acids | 0.5% |
| Unknowns | 2.2% |

Typical Saponification Products of Lanolin

If lanolin is saponified using base and analyzed the following composition is typical

| FATTY ACID | |
|---|---|
| Aliphatic | 31.1% |
| Alpha-hydroxy | 13.8% |
| Omega-hydroxy | 2.6% |
| Unsaturated | 2.4% |
| Others | 1.1% |
| SUBTOTAL | 51.0% |

| ALCOHOLS | |
|---|---|
| Cholesterols | 19.6% |
| Lanosterols | 12.6% |
| Aliphatic | 8.0% |
| 1,2 diols | 4.1% |
| Others | 2.7% |
| UNSPECIFIED | 2.0% |
| SUBTOTAL | 49.0% |

Lanolin has the following Typical Analysis

| Color (Gardner) | 12 max. |
|---|---|
| Free Fatty Acid (as Oleic) | 1.5% max. |
| Iodine Value (Hanus) | 18–36 |
| Melting Range | 38°–42° C. |
| Water | 0.25% max. |
| Residue on Ignition | 0.1% max. |

Guerbet Alcohols

Guerbet Alcohols are regiospecifically beta branched alcohols. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The Guerbet reaction gives very specific branching, on the second carbon from the hydroxyl group. This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching (between 1 and 28%) the Guerbet process gives essentially 100% product. Guerbet alcohols that are the reaction product of one specific raw material alcohol will result in a so-called "homo-Guerbet". In this case R and R' are identical. If the starting alcohols used in the Guerbet reaction are of differing molecular weights a so-called "hetero-Guerbet" results. This type of Guerbet has a mixed distribution of all possible combinations of alcohols. For this reason R and R' in the generic formula may be the same or different.

Guerbet alcohols are available commercially from Sassol Corporation, formerly called Condea Vista. Guerbet alcohols conform to the following structure:

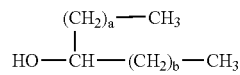

wherein;

a in an integer ranging from 3 to 11;

b in an integer ranging from 5 to 19.

It should be clear from the reaction sequence that the Guerbet alcohol is reacted into the ester, making a new-branched ester and leaving a free lanolin alcohol. The resulting composition contains a branched ester and an alcohol that is derived from the lanolin. The selection of the Guerbet and wax determines the melting point and the degree of hardness of the wax. This is very important in a variety of applications, like automotive polishes, and personal care products like lipsticks.

The products are applied to the skin or skin by rubbing. The products may be used as is or formulated into an emulsion with a surfactant and water using emulsification techniques known to those skilled in the art. Vitamins, fragrances, sunscreens and the like can also be added.

Guerbet Examples

| Example | Designation | a | b |
|---|---|---|---|
| 1 | Guerbet C12 | 3 | 5 |
| 2 | Guerbet C16 | 5 | 7 |
| 3 | Guerbet C20 | 7 | 9 |
| 4 | Guerbet C24 | 9 | 11 |
| 5 | Guerbet C28 | 11 | 13 |
| 6 | Guerbet C32 | 13 | 15 |
| 7 | Guerbet C36 | 15 | 17 |
| 8 | Guerbet C40 | 17 | 19 |

General Procedure

The compounds of the present invention are prepared by the transesterification reaction of the lanolin and the Guerbet alcohol. The reaction is carried out with a molar ratio of 0.5:1 lanolin to Guerbet to 1:0.5 ratio with a preferred mole ratio of 1:1. The wax and the polymer are added to a suitable reaction vessel under agitation. The two are heated to 160–250° C. with a preferred temperature of between 180–200° C. An esterification catalyst selected from para toluene sulfonic acid, tin oxylate, sulfuric acid and other esterification catalysts. The reaction is conducted at 180 to 200° C. for three to eight hours. During that time alkyl alcohol is generated. This alcohol has found to be a critical element to the composition's functionality. Its presence allows for better coupling of the product when put in formulations.

To 400.0 grams of lanolin is added the specified number of grams of the specified Guerbet alcohol. Next is added the catalyst. The reaction is conducted at 180 to 200° C. for eight hours. During that time lanolin alcohol is generated. This alcohol has found to be a critical element to the composition's functionality.

| | Guerbet Alcohol | |
|---|---|---|
| Example | Example | Grams |
| 9 | 1 | 188.0 |
| 10 | 2 | 244.0 |
| 11 | 3 | 300.0 |
| 12 | 4 | 356.0 |
| 13 | 5 | 412.0 |
| 14 | 6 | 468.0 |
| 15 | 7 | 524.0 |
| 16 | 8 | 580.0 |
| 17 | 1 | 212.0 |
| 18 | 2 | 200.0 |
| 19 | 3 | 250.0 |
| 20 | 4 | 300.0 |
| 21 | 5 | 385.0 |
| 22 | 6 | 428.0 |
| 23 | 7 | 524.0 |
| 24 | 8 | 530.0 |

The products of the invention all are cosmetically elegant. By cosmetically elegant is meant that there is no stickiness, or tack to the products. All products were very effective on the skin providing good emolliency and improving the consumer perception of healthy skin. 90% of the panelists tested preferred the lanolin products of the present invention to lanolin alone. 80% preferred the products of the present invention over the pure Guerbet alcohol when asked which product improved their skin more.

The compounds of the present invention were found to be non-irritating to skin, making them ideal for personal care applications.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A composition made by the trans esterification reaction of a Guerbet alcohol conforming to the following structure:

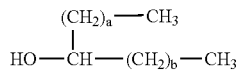

wherein;
 a is an integer ranging from 3 to 11;
 b is an integer ranging from 5 to 19, with the proviso that b=a+2;
 and lanolin, wherein said trans esterification reaction is carried out at a temperature of between 180° C. and 200° C.

2. A composition of claim 1 wherein a is 3 and b is 5.

3. A composition of claim 1 wherein a is 7 and b is 9.

4. A composition of claim 1 wherein a is 9 and b is 11.

5. A composition of claim 1 wherein a is 11 and b is 13.

6. A process for conditioning hair and skin, which comprises contacting the hair or skin with an effective conditioning concentration of a composition made by the esterification reaction of a Guerbet alcohol conforming to the following structure:

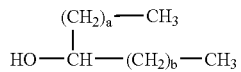

wherein
 a is an integer ranging from 3 to 11;
 b is an integer ranging from 5 to 19, with the proviso that b=a+2;
 with lanolin, wherein said esterification reaction is carried out at a temperature of between 180° C. and 200° C.

7. A process of claim 6 wherein a is 3 and b is 5.

8. A process of claim 6 wherein a is 7 and b is 9.

9. A process of claim 6 wherein a is 9 and b is 11.

10. A process of claim 6 wherein a is 11 and b is 13.

* * * * *